United States Patent [19]
Alvan et al.

[11] 3,985,873
[45] Oct. 12, 1976

[54] SOLUTION CONTAINING TRIMETHOPRIM, SULFACETAMIDE AND POLYMYXIN

[75] Inventors: George E. Alvan; Elvin A. Holstius, both of Greenville, N.C.

[73] Assignee: Burroughs Wellcome Co., Research Triangle Park, N.C.

[22] Filed: Apr. 18, 1975

[21] Appl. No.: 569,412

Related U.S. Application Data

[63] Continuation of Ser. No. 428,918, Dec. 27, 1973, abandoned.

[52] U.S. Cl. ............................ 424/177; 424/228; 424/251
[51] Int. Cl.² ................ A61K 37/00; A61K 31/63; A61K 31/505
[58] Field of Search .................... 424/229, 177, 228

[56] References Cited
UNITED STATES PATENTS
3,881,003  4/1975  Rehm ............................ 424/229

OTHER PUBLICATIONS

Montgomerie et al. – Chem. Abst. vol. 79 (1973) p. 15747d.

Wilson et al. – American Drug Index (1970) pp. 451 and 534.

*Primary Examiner*—Sam Rosen
*Attorney, Agent, or Firm*—Donald Brown

[57] ABSTRACT

Ophthalmic solution suitable for treatment of microbial, especially bacterial, infections of and around the eye containing sulfacetamide, a medicinally or pharmaceutically acceptable water soluble mono salt of trimethoprim, a medicinally or pharmaceutically acceptable water soluble salt of polymyxin, especially polymyxin B, and water, the solution having a pH in the range of 4.5 to 6.5 with 5 to 6 being preferred.

10 Claims, No Drawings

SOLUTION CONTAINING TRIMETHOPRIM, SULFACETAMIDE AND POLYMYXIN

This is a continuation of application Ser. No. 428,918, filed on Dec. 27, 1973, now abandoned.

BACKGROUND OF THE DISCLOSURE

The present invention relates to an aqueous ophthalmic preparation and more particularly to an aqueous ophthalmic solution useful for treating antimicrobial infections and particularly bacterial infections of and about the eye.

In particular, the aqueous ophthalmic solution of this invention contains 2,4-diamino-5-(3',4',5'-trimethoxybenzyl) pyrimidine (known as trimethoprim), N'-Acetylsulfanilamide, sometimes called p-aminobenzenesulfonacetamide, (hereinafter called sulfacetamide) and polymyxin, preferably polymyxin B.

Trimethoprim is a well known antimicrobial agent and has found particular utility in the treatment of various bacterial and protozoal infections, see U.S. Pat. No. 2,909,522. Trimethoprim has also been used in the past in combination with various sulphonamides as a sulphonamide potentiator.

Sulfacetamide is also a well known antimicrobial agent (see p. 13 of The Merck Index, Eighth Edition, 1968) and has found particular utility in the treatment of bacterial infections.

Polymyxin, a generic name for antibiotics (see p. 848 of The Merck Index, Eighth Edition, 1968) is useful as an antimicrobial agent and has particularly useful activity in the treatment of gram-negative bacterial infections.

During the last few years, it became apparent that a new and improved broad spectrum ophthalmic solution was needed for the treatment of the multitude of bacterial infections encountered in the eye.

A new solution in order to be useful as an antibacterial for ophthalmic use had to remain stable for long periods of time (useful shelf life), not lose its potency (a known characteristic of polymyxin under certain conditions), remain as a clear solution, that is not discolor, e.g., as a result of oxidation of the sulphonamide (a known characteristic of sulfacetamide base in solution), not form insoluble substances or complexes because of the combining of trimethoprim, a sulphonamide, and/or a polymyxin in the same solution (a known difficulty encountered with trimethoprim and certain sulphonamides), and also not be especially irritating to the eye (e.g., because of the pH of the solution, or because of the use of organic solvents which are not particularly acceptable to the eye).

As a result of this invention there is provided an ophthalmic solution meeting the stringent criteria set forth above as well as a solution having a broad spectrum antimicrobial, especially antibacterial activity.

According to the present invention there is provided an aqueous ophthalmic solution which has been discovered to meet the stringent criteria set forth above, said ophthalmic solution containing (1) chemotherapeutic and especially antibacterial effective treatment amount of sulfacetamide in solution; (2) a water soluble, pharmaceutically acceptable effective sulfacetamide potentiating amount of mono salt of trimethoprim, preferably a mono acid addition salt of trimethoprim, in solution; (3) a chemotherapeutic and especially an antibacterial effective antibacterial treatment amount of a water soluble pharmaceutically acceptable salt of polymyxin, especially polymyxin B, in solution; and (4) water, the solution having a pH in the range of 4.5 to 6.5 with a pH of 5 to 6 being preferred.

In addition, the present invention may include isotonic agents such as sodium chloride to make the solution isotonically compatable with the fluids of the eye as well as pharmaceutically or medicinally acceptable pH adjusting agents.

Further optional ingredients such as preservatives or viscosity increasing and film forming agents to prolong mucus membrane contact time, etc., may be included so long as they do not detrimentally effect the desirable properties of the solution.

In accordance with this invention the ophthalmic solution contains from about 0.05 % to 0.66 % w/v of sulfacetamide (as base) with 0.10 to 0.50 % w/v of sulphacetamide (as base) being preferred, from about 0.005 to 1.0 % w/v of trimethoprim (as base) with 0.010 to 0.5 % w/v of trimethorpim (as base) being preferred, from about 0.01 to 0.3% w/v of polymyxin (as base) with .05 to 0.15% w/v of polymyxin being preferred. The remainder of the solution is water although from about 0.02 to 1 % w/v of a pH adjusting agent may be incorporated therein with about 0.03% to 0.07% of a pH adjusting agent being preferred.

Substances which can be used as pharmaceutically or medicinally acceptable acids to form water soluble pharmaceutically acceptable mono salts of trimethoprim are for example, pharmaceutically acceptable mineral acids such as sulfuric, phosphoric, hydrochloric, hydrobromic, hydroiodic, as well as pharmaceutically acceptable organic acids such as pharmaceutically acceptable carboxylic acids preferably having between 1 to 20 carbon atoms and most preferably 1 to 10 carbon atoms; e.g., tartaric, citric, lactic, embonic, salicyclic, glutamic, glutaric, naphthoic, acetic, and ethylenediamine-tetra acetic acid and other pharmaceutically acceptable organic acids such as methane sulphonic acid. The acids used herein to form the salt or the salts of trimethoprim potentiator must be stronger acids, i.e., have a lower pKa than the sulphonamide. At present, the preferred acids are lactic acid, or sulfuric acid, both being conveniently accessible and acceptable for the practice of this invention.

The water soluble pharmaceutically acceptable salts of trimethoprim may be formed by the reaction of trimethoprim and a pharmaceutically acceptable acid. A pharmaceutically acceptable mono acid addition salt of trimethoprim or a mono acid addition salt of a pharmaceutically acceptable acid and trimethoprim is defined herein as a salt consisting of mono-protonated trimethoprim and an anion of a pharmaceutically acceptable acid. The pH of the solution and the Pka's of the pharmaceutically acceptable acid and trimethoprim will determine their respective ionization status. Although it is well known that the chemotherapeutic, especially the antibacterial, activities of the sulphonamides and of trimethoprim are mutually enhanced when these agents are acting together, for the purposes of this invention, trimethoprim is herein sometimes referred to as a sulfacetamide potentiator.

The present invention is not limited to a particular polymyxin and accordingly all of the polymyxins disclosed on page 848 of The Merck Index, 8th Edition, 1968, as well as pages 278 and 279 which disclose colestin (polymyxin E), are incorporated herein by reference hereto, although for the purpose of this invention polymyxin B is preferred.

In the practice of this invention, the polymyxin is utilized as a water soluble pharmaceutically acceptable or medicinally acceptable salt. Conveniently, the polymyxin may be used as a sulfate salt or a hydrochloric acid salt in the solution, e.g., polymyxin B sulfate.

The polymyxin as a salt may be conveniently dissolved in the solution at room temperature without stirring although stirring may be used.

The sulfacetamide and trimethoprim as a salt may be conveniently dissolved in the solution at elevated temperatures of 85° to 90° C with stirring although lower temperatures may also be used. This may be accomplished readily either by adding sulfacetamide to the water with or without the salt of trimethoprim present.

It is preferable to insure that the pH of the solution to which the sulfacetamide or the salt of trimethoprim is added in any order is maintained at a volume and pH sufficient to prevent formation of an insoluble salt.

Usually the ratio of sulfacetamide to trimethoprim as base or polymyxin as base, e.g., polymyxin B, useful to obtain a therapeutic effect (e.g., to treat bacterial infections) is in the order of 5:1 (w/w), although ratios being between 10:1 to 0.1:1 (w/w) are useful, and in certain cases it may be as high as between 20:1 to 0.1:1 (w/w).

In practice the preferred amounts of polymyxin per 100 ml. of solution is about 500,000 to 2,000,000 units with about 1,000,000 to 1,200,000 units being most preferred. 1,200,000 units of polymyxin represents about .15 grams of polymyxin B in terms of base.

As noted previously, the pH of the solution is between 4 and 6.5 with a range of 4.5 to 5.5 being preferred and a pH of 5.0 ± 0.3 being most preferred to meet the criteria set forth herein.

Suitable pH adjusting agents which may be included in the solution include the pharmaceutically acceptable acids previously mentioned such as hydrochloric acid or under certain conditions may include pharmaceutically acceptable bases such as sodium hydroxide, potassium hydroxide, etc.

The amount of pH adjusting agent normally used if needed would be from about 0.02 to 1.0 percent w/v with 0.03 percent to 0.07 percent being preferred.

As previously mentioned the solution may also contain isotonic agents such as sodium chloride with an amount in the range of 0.3 to 1.2 grams/100 ml of solution being useful and with an amount between 0.6 to 1.0 grams/100 ml of solution being preferred.

Other optional ingredients such as preservatives, e.g., THIMEROSAL made by Eli Lilly and Company may also be included. In addition, viscosity and film forming agents such as Methocel 65 HG, 4000 cps may also be included to prolong contact of the solution with the mucous membrane.

It also may be desirable in certain cases to add local anaethesia components or other ingredients to enhance stability if needed.

Accordingly, it should again be understood that other ingredients may be added so long as these additional ingredients do not detract from the desirable properties of the solution.

The quantity of the ophthalmic solution of this invention which can be administered to a host mammal or animal, e.g., human, rabbit, etc., for the treatment of microbial and especially bacterial infections varies according to the species of the host, its size, its age, general condition of health and severity and type of infection.

The solution of this invention would normally be packaged in conventional ophthalmic dispensing containers and would normally be administered around the eye as 0.02 to 0.1 ml drops containing the ingredients in the concentration set forth above.

Normally, one or two drops of the solution would be administered 1 to 4 times daily. For example, in the treatment of bacterial infections around the eye in man, animals, e.g., rabbits, (e.g., for conjunctivitis), from a solution containing 1 mg/ml of trimethoprim base, 5 mg/ml of sulfacetamide, and 10,000 u/ml of polymyxin B as base, two 0.07 ml drops may be administered 2 to 4 times daily.

The solution of this invention has shown in invitro tests wide antibacterial inhibitory activity against various bacteria, normally found causing infections around the eye at dilutions of at least 1:300 (which is likely to occur in the eye because of the eye fluids). Among the bacteria causing infections around the eye and in which inhibitory activity has been found are the following: *St. pyogenes, Staph. aureus, N. gonorrhoeae, Morax. phenylpyrovich, Morax. nonliquifaciens, St. pneumoniea I, Ps. aeruginosa* and *H. influenzae*.

In 12 month storage tests, with the solution of the invention, satisfactory potencies for all active ingredients has been observed at 5° C and 25° C.

It should be understood that the ophthalmic solution of this invention is sterile and that the water used in its preparation is preferably distilled water.

As used herein the term infections of and around the eye is meant to include external bacterial infections of the eye, due to susceptible organisms and includes the following conditions: acute and chronic conjunctivitis, pinkeye, infected sockets, corneal ulcers, keratitis, episcleritis, blepharitis. The solution of the present invention is also useful as an adjunct to surgery in dacryocystitis; and prophylactically, before or after ophthalmic surgery and following serious eye injuries or removal of foreign bodies.

The following examples further illustrate this invention. It is to be noted that all temperatures are in degrees centigrade, unless otherwise specified and where no temperature is given for the mixing of the ingredients or to prepare the salt, room temperature is the temperature at which the ingredients were mixed or at which temperature the salt was formed.

Obviously higher or lower temperatures may be used depending on how quickly it is desired for the mixing or the formation of the salt to take place as well known by those skilled in the art.

All percentages in this application mean w/v percentages, unless otherwise specified.

EXAMPLE 1

Ophthalmic Solution

| | |
|---|---|
| Sulfacetamide | 0.50 g. |
| Trimethoprim Hemisulfate Monohydrate equivalent to | 0.123 g. |
| Trimethoprim Base | 0.10 g. |
| Polymyxin B Sulfate | 1,200,000 u.(.15 g.) |
| Thimerosal - Preservative | 0.001 g. |
| Sodium Chloride | 0.83 g. |
| Water for Injection, q.s. | |
| | 100.00 ml. |

General Preparation

Added the polymyxin B sulfate to 10 ml. waer. Allowed it to dissolve without stirring.

In a separate container, dissolved the trimethoprim hemisulfate monohydrate and sulfacetamide in 35 ml. water heated to 85° – 90° C. Added 35 ml. cold water. Mixed continuously. Added the sodium chloride.

To the preceding solution, added the polymyxin B sulfate solution. Rinsed container with 10 ml. water and added rinsing to bulk solution. Added THIMEROSAL. Brought solution to near final volume with water. Cooled solution to room temperature (25° C.). Checked pH and adjusted with 2N sodium hydroxide solution to a pH of 5.0 ± 0.2.

Adjusted to final volume with water. Mixed for 10 minutes and rechecked pH. Passed solution through a suitable filter. Filled 10 ml. portions of solution into amber bottles. Applied suitable closures. Sterilized bottles by autoclaving at 121° C. for 20 minutes.

Alternately, the solution may be sterilized by filtration through a suitable sterile filter and aseptically subdivided into sterile bottles.

EXAMPLE 2

Ophthalmic Solution

| | |
|---|---|
| Sulfacetamide | 0.50 g. |
| Trimethoprim Hemisulfate Monohydrate equivalent to | 0.123 g. |
| Trimethoprim Base | 0.10 g. |
| Polymyxin B Sulfate (includes 20% overage) | 1,200,000 u.(.15 g.) |
| Thimerosal | 0.001 g. |
| Sodium Chloride | 0.83 g. |
| Water for Injection, q.s. | 100.00 ml. |

General Preparation

Added the polymyxin B sulfate to 10 ml. water. Allowed drug to dissolve without stirring.

In a separate container, dissolved the trimethoprim hemisulfate and the sulfacetamide in 70 ml. water heated to 50° C. Added the sodium chloride.

To the preceding solution, added the polymyxin B sulfate solution. Rinsed container with 10 ml. water and added rinsing to bulk solution. Added the THIMEROSAL. Brought solution to near final volume with water. Cooled solution to room temperature (25° C.).

Checked pH and adjusted with 2N sodium hydroxide solution to a pH of 5.0 ± 0.2.

Adjusted to final volume with water. Mixed for 10 minutes and rechecked pH. Passed solution through a suitable filter. Filled 10 ml. portions of solution into amber bottles. Applied closures. Sterilized containers with steam under pressure at 121° C. for 20 minutes.

NOTE: Under General Preparation, water refers to water for injection.

EXAMPLE 3

Ophthalmic Solution

| | |
|---|---|
| Sulfacetamide | 0.05 g. |
| Trimethoprim Lactate equivalent to trimethoprim base | 0.01 g. |
| Polymyxin B Sulfate (includes 20% excess) | 1,200,000 u.(.15 g.) |
| Water for Injection, q.s. | 100.00 ml. |

EXAMPLE 4

Ophthalmic Solution

| | |
|---|---|
| Sulfacetamide | 0.50 g. |
| Trimethoprim Lactate equivalent to trimethoprim base | 0.10 g. |
| Polymyxin B Sulfate (includes 20% excess) | 1,200,000 u.(.15 g.) |
| Water for Injection, q.s. | 100.00 ml. |

EXAMPLE 4 ophthalmic Solution

| | |
|---|---|
| Sulfacetamide | 0.50 g. |
| Trimethoprim Lactate equivalent to | 0.130 g. |
| Trimethoprim Base | 0.10 g. |
| Polymyxin B Sulfate (includes 20% excess) | 1,200,000 u.(.15 g.) |
| Water for Injection, q.s. | 100.00 ml. |

We claim:

1. A clear aqueous pharmaceutically acceptable solution capable for use as an ophthalmic antibacterial preparation, the solution being at a pH of 4.0 to 6.5 and the solution containing 0.05 to 0.66 % w/v of sulfacetamide, 0.01 to 0.50% w/v of trimethoprim in the form of a pharmaceutically acceptable water soluble salt, and 0.01 to 3% w/v of polymyxin in the form of a pharmaceutically acceptable water soluble salt and water.

2. A solution according to claim 1 in which the polymyxin is polymyxin B.

3. A solution according to claim 1 in which the polymyxin is polymyxin E.

4. A method of treating bacterial infections of and around the eye of a patient which comprises administering to the patient an effective antibacterial treatment amount of the solution of claim 1.

5. A method according to claim 4 in which the patient is a mammal.

6. A method according to claim 5 in which the patient is a human.

7. A method according to claim 6 in which the polymyxin is polymyxin B,

8. A solution according to claim 1 in which the pH of the solution is about 4.5 to 5.5.

9. A solution according to claim 1 in which the pH of the solution is about 5.0 ± .3.

10. The solution of claim 8 in which the polymyxin is polymyxin B.

* * * * *